(12) United States Patent
Shlomovitz

(10) Patent No.: US 8,323,224 B2
(45) Date of Patent: Dec. 4, 2012

(54) ANKLE FOOT ORTHOSIS

(75) Inventor: Tal Shlomovitz, Givataim (IL)

(73) Assignee: Ya'ad Advanced Orthopedics Ltd., Tel Aviv (IL)

( * ) Notice: Subject to any disclaimer, the term of this patent is extended or adjusted under 35 U.S.C. 154(b) by 685 days.

(21) Appl. No.: 12/423,218

(22) Filed: Apr. 14, 2009

(65) Prior Publication Data

US 2009/0198166 A1 Aug. 6, 2009

Related U.S. Application Data

(63) Continuation-in-part of application No. 11/757,697, filed on Jun. 4, 2007, now abandoned.

(51) Int. Cl.
*A61F 5/00* (2006.01)
*A61F 13/00* (2006.01)
(52) U.S. Cl. .................. 602/27; 602/5; 602/23; 602/65
(58) Field of Classification Search .............. 602/27–29, 602/23, 5; 128/882; 36/140
See application file for complete search history.

(56) References Cited

U.S. PATENT DOCUMENTS

| | | | |
|---|---|---|---|
| 2,949,111 A | 8/1960 | Veikko | |
| 3,680,549 A | 8/1972 | Lehneis et al. | |
| 3,805,773 A * | 4/1974 | Sichau | ............. 602/28 |
| 3,916,886 A | 11/1975 | Rogers | |
| 4,672,955 A | 6/1987 | Cooper | |
| 5,897,515 A | 4/1999 | Willner et al. | |
| 6,102,881 A | 8/2000 | Quackenbush et al. | |
| 6,361,517 B1 | 3/2002 | Slinger | |
| 6,790,193 B2 | 9/2004 | Wellershaus et al. | |
| 6,945,947 B2 | 9/2005 | Ingimundarson et al. | |
| 2007/0197948 A1 | 8/2007 | Ingimundarson et al. | |

FOREIGN PATENT DOCUMENTS

WO WO0135876 5/2001

\* cited by examiner

*Primary Examiner* — Kim M Lewis
(74) *Attorney, Agent, or Firm* — The Law Office of Michael E. Kondoudis

(57) ABSTRACT

Disclosed is an ankle foot orthotic device for assisting a user during gait. The device comprises: a foot support having a shape and size configured to the plantar aspect of a user foot, the foot support having a forward portion and a rearward portion and a heel plate coupled to an upper surface of the rearward portion. The device further comprises: an upper rod having a longitudinal axis and a lower end connected to an offset and a lower rod having: a longitudinal axis; a lower end connected to the heel plate; and an upward end connected to the offset.

18 Claims, 20 Drawing Sheets

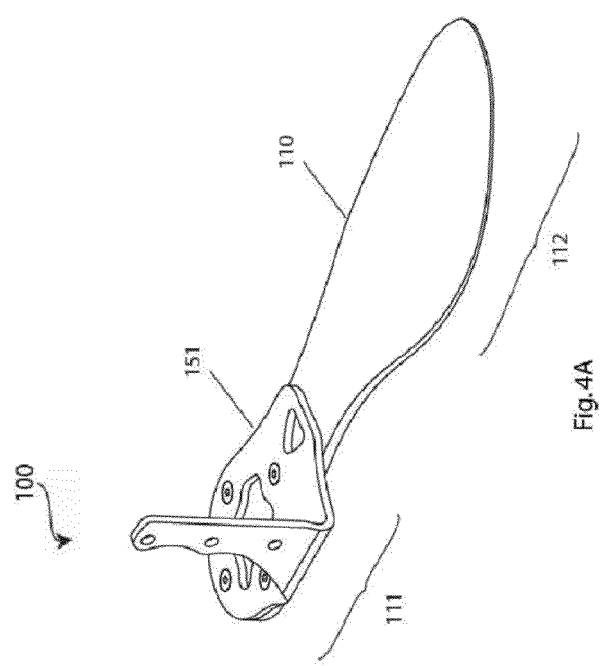
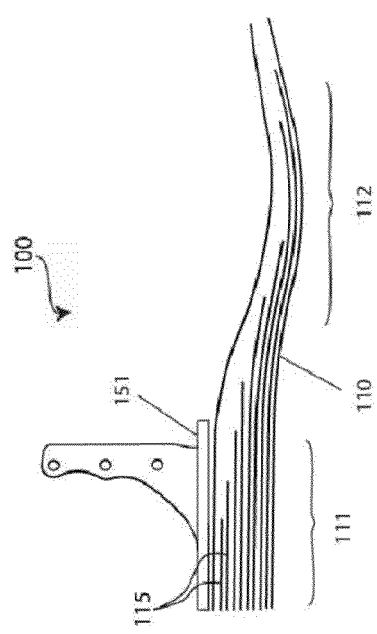

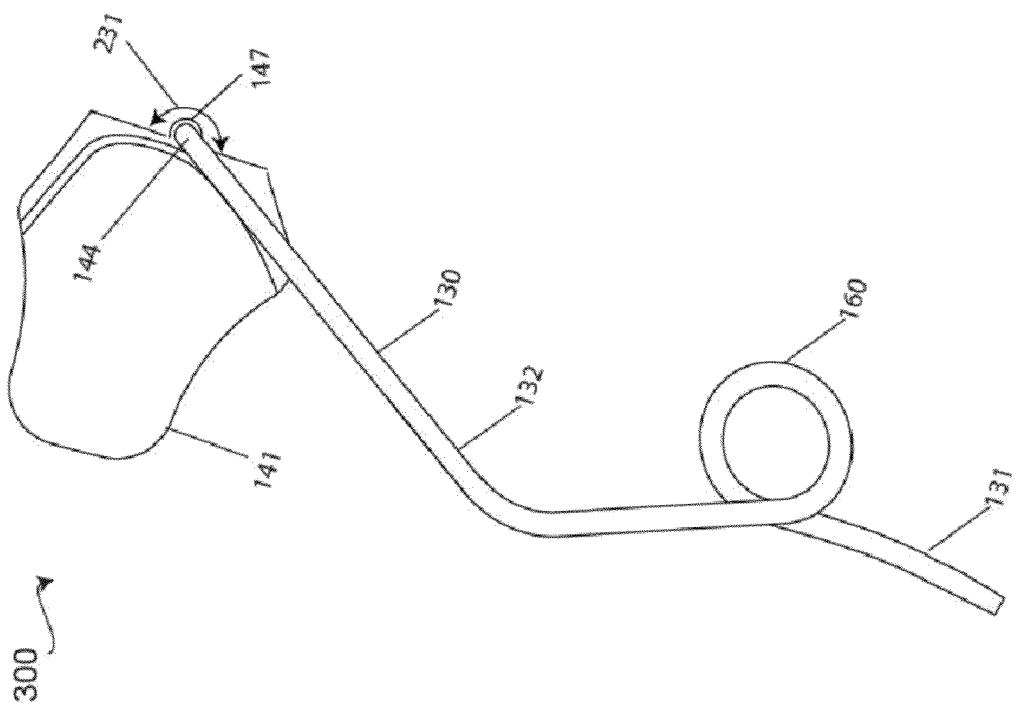

ANKLE FOOT ORTHOSIS

RELATED APPLICATION

This application is a Continuation in Part of U.S. application Ser. No. 11/757,697, "An Ankle Foot Orthosis Device", filed 4 Jun. 2007; the content of which is incorporated by reference as if fully set forth herein.

FIELD AND BACKGROUND OF THE INVENTION

The present invention, in some embodiments thereof, relates to orthoses and, more particularly, but not exclusively, to an ankle foot orthosis.

Drop foot, also known as steppage gait, is a condition in which there is a deficit in pivoting the foot upward toward the anterior of the tibia, herein dorsiflexion, due to neurologic and/or muscular malfunction.

To prevent tripping during swinging forward, herein swing phase of gait, the affected leg must be lifted high off the ground and dropped into place in front of the other foot, referred to as a steppage gait.

In "swing phase" of gait, the drop foot remains in the "dropped", herein plantiflexed position and often barely clears the ground during the swing phase. As a result, the foot may catch on low lying debris, rocks or even an edge of a pavement stone, causing the person to trip and fall.

A fall, particularly in an osteoporotic older person, can result in life-threatening bone fractures, immobility, and, due to the resultant sedentary life style, an early demise.

Surgical treatment, when applicable, includes muscle transfers and/or nerve implantation; the latter presently limited to nerve lesions near the spinal nerve root.

Conservative therapy includes fitting the user with an ankle foot orthosis (AFO); which lifts the foot with respect to the leg during swing phase of the gait, thereby substantially allowing the foot to clear the ground.

There are aspects of the phases gait that may be beneficial to a user afflicted by drop foot when properly addressed by an AFO; for example pronation and supination of the foot.

Pronation refers to inter alia, the forefoot assuming a substantially parallel position to the ground whereby the foot flexibly adapts to the angle and/or terrain of the ground.

Supination refers to inter alia, the forefoot assuming an angled position to the rear foot in whereby the forefoot forms, what is referred to as a "locked position". The locked position of the forefoot during supination allows the foot to act as a lever to aid in propulsion associated with the toe off phase of gait.

In the drop foot condition, even with fully non-functional intrinsic and extrinsic foot muscles, the foot assumes "passive" positions of pronation and supination.

For example, when the right leg is in swing phase and through heel contact, the right foot is in preparation to pronate upon contact with the ground.

As the right foot becomes fully planted on the ground, in what is referred to as the "foot flat" position, the left leg is in swing phase while the left side of the pelvis circumducts toward the sagittal body plane. The left pelvic circumduction causes a supination in the right foot, with the supination continuing through right foot toe off.

Following toe-off, the right foot again assumes a position of pronation in preparation for heel contact and foot flat phases of the gait cycle.

To aid in the above-noted passive cycle of pronation and supination in a leg afflicted with drop foot, a natural tilt occurring between the foot plate and vertical support of a typical AFO could aid the affected foot in supination and pronation.

For example, when the AFO connection between the foot plate and vertical support is rigid and unyielding, supination and pronation forces may be transferred to the foot rather than the ankle and/or mid tarsal joints that provide some of the movement required in pronation and supination.

With the movement transferred to the foot, rather than the above-noted joints, the foot, and particularly the heel, may swing in the support plate and tend to become chaffed and sore.

Such limitation of motion may reduce the ability of the foot to act as a shock absorber during heel-strike through foot flat portions of the gait cycle. With the decrease in foot shock absorption, the shock forces of heel strike are translated up the leg to the knee and hip joints, leading to osteoarthritis, pain, and possible limitation of range of motion in the knee and hip.

Additionally, the shock forces absorbed may be translated to the lower back, resulting in lower back pain and possibly disc herniation, particularly in the lumbar spinal area.

Further, during the swing phase of the above-noted left foot, the circumduction of the pelvis translates into rotatory forces on the right foot that is planted on the ground, thereby creating the above-noted supination, that should translate into a torque of the ankle joint and/or mid tarsal joint wherein the right foot tibia circumducts away from the sagittal body plane.

If the foot plate maintains an intrinsic rigidity during gait, the midtarsal area of the foot may be forced to passively supinate against the rigid plate and/or rearfoot, creating undue stress on the midtarsal joint which can result in pain, arthritis and limitation of motion in the midtarsal joint.

Background art, incorporated herein in their entirety by reference, include the following U.S. Pat. Nos.:

1. U.S. Pat. No. 3,916,886, which teaches a preformed drop foot brace;
2. U.S. Pat. No. 4,672,955, which teaches bands formed of curable composite material;
3. U.S. Pat. No. 5,897,515, which teaches an ankle-foot orthosis made of a carbon fiber reinforced material;
4. U.S. Pat. No. 6,102,881, which teaches an upper support bearing against the rear lower leg and a lower support bearing against the rear heel;
5. U.S. Pat. No. 6,361,517, which teaches a foot lift assist comprising an elastic cord anchored at a person's hip by a belt;
6. U.S. Pat. No. 6,790,193, which teaches a dorsal leg shell affixed to a user calf;
7. U.S. Pat. No. 3,680,549 (Lehnels et al);
8. U.S. Pat. No. 2,949,111 (Veikko Samuli Ruotoistenmaki, Vaasankatu);
9. U.S. Pat. No. 6,945,947 B2 (Ingimundarson et al);

Additional background art, incorporated herein in their entirety by reference, include the following U.S. patent applications:

1. Patent Publication No. WO/0135876, teaches a spring attached to the front side of a wearer's leg in a manner that allows sliding of the spring longitudinally; and
2. U.S. Patent Application Publication No. 2007/0197948 A1.

SUMMARY OF THE INVENTION

The present invention, in some embodiments thereof, relates to orthoses and, more particularly, but not exclusively, to an ankle foot orthosis.

According to an aspect of some embodiments of the present invention there is provided an ankle foot orthotic device for assisting a user during gait. The device comprises: a foot support having a shape and size configured to the plantar aspect of a user foot, the foot support having a forward portion and a rearward portion and a heel plate coupled to an upper surface of the rearward portion. The device further comprises: an upper rod having a longitudinal axis and a lower end connected to an offset and a lower rod having: a longitudinal axis; a lower end connected to the heel plate; and an upward end connected to the offset.

In some embodiments of the invention, the offset comprises a curved member.

In some embodiments of the invention, the curved member curves substantially around a sagittal plane with respect to the foot support.

In some embodiments of the invention, the offset is configured to allow relative movement along a coronal plane with respect to the foot support during user weight bearing.

In some embodiments of the invention, the offset is configured to allow relative movement along a sagittal plane with respect to the foot support during user weight bearing.

In some embodiments of the invention, the device includes a cuff connected to an upper end of the upper rod, the cuff configured to press against at least a portion of an anterior tibia.

In some embodiments of the invention, the cuff is rotatably connected by a rotatable hinge to an upper end of the upper rod.

In some embodiments of the invention, the rotatable hinge is configured to allow a swinging motion in the cuff along a sagittal plane with respect to the longitudinal axis of the upper rod.

In some embodiments of the invention, the foot plate comprises a flexible material.

In some embodiments of the invention, the heel plate is substantially rigid such that when the rear end of the rigid heel plate rises with respect to the foot support, and the forward portion is planted on a support surface, bending of the rigid heel plate is transferred beyond the front boundary of the heel plate.

In some embodiments of the invention, when the forward portion is no longer in contact with the support surface, energy of the bending is transferred such that a sagittal axis passing through the forward portion becomes substantially aligned with a sagittal axis passing through the rearward position.

According to another aspect of some embodiments of the present invention there is provided An ankle foot orthotic device for assisting gait, the device comprising: a rigid heel plate having a shape and size configured to encompass at least a portion of the plantar aspect of a user heel, the heel plate having a lower surface, a rod extending upward from the rigid heel plate, a cuff connected to an upper end of the rod, the cuff configured to press against at least a portion of an anterior tibia, a foot support having a shape and size configured to encompass at least a portion of the plantar aspect of a user foot, the foot support including: a forward flexible portion, a rearward portion having an upper surface rigidly connected to the lower surface of the rigid heel plate, such that when a rear end of the heel plate rises with respect to a sagittal axis of the foot support, and the forward portion is planted on a support surface, energy of bending is transferred to the forward flexible portion.

In some embodiments of the invention, the rod includes a spring offset configured to transfer forces generated between the rod and the foot support to the foot support.

In some embodiments of the invention, the ankle foot orthotic device is provided in a kit comprising modular components comprising different sizes comprising: the foot support, the rigid heel plate, the rod, and the cuff.

In some embodiments of the invention, the lower surface of the rigid heel plate is configured to connect to an upper surface of a rearward portion of the foot support.

In some embodiments of the invention, the rod is configured to connect to the rigid heel plate, the rod having an upper end configured to have a length sufficient to reach a mid to upper portion of a user tibia.

In some embodiments of the invention, the rod includes: a portion extending upwardly from the heel plate and having an upward end connected to an offset, and an upper rod having a lower end connected to the offset such that the lower end is offset by a distance from the upper end.

In some embodiments of the invention, the offset is configured to allow relative movement along a coronal plane with respect to the foot support.

In some embodiments of the invention, the offset is configured to allow relative movement along a sagittal plane with respect to the foot support.

According to still another aspect of some embodiments of the present invention there is provided ankle foot orthotic device for assisting gait, the device comprising: a foot support having a shape and size configured to the plantar aspect of a user foot, the foot support having a rearward portion and a flexible forward portion, a rigid heel plate coupled to an upper surface of the rearward portion, wherein: when a rear end of the heel plate rises with respect to the foot support, and the forward portion is planted on a support surface, energy of bending is transferred beyond the front boundary of the heel plate, and when the forward portion is no longer in contact with the support surface, the energy of the bending is transferred such that a sagittal axis passing through the forward portion becomes substantially aligned with a sagittal axis passing through the rearward portion, an upper rod having a longitudinal axis and a lower end connected to an offset, a cuff rotatably connected to an upper end of the upper rod with a rotatable hinge, the rotatable hinge configured to allow a swinging motion in the cuff along a sagittal plane with respect the longitudinal axis of the upper rod, a lower rod having a longitudinal axis extending upwardly from the heel plate and having an upward portion connected to the offset, wherein the offset is configured to allow at least one of: relative movement along a coronal plane with respect to the foot support, and relative movement along a sagittal plane with respect to the foot support.

According to an additional aspect of some embodiments of the present invention there is provided a method of fabricating an ankle foot orthosis device for assisting gait, the method comprising: fabricating a foot support configured to at least partially encompass the plantar surface of a user foot, attaching to an upper surface of the foot support a rigid heel support configured to at least partially encompass the plantar surface of a user heel, bending an elongate bar to include an offset between an upper end and a lower end of the elongate bar, rigidly attaching a lower portion of the elongate bar to the rigid heel support, and rotatably attaching, to an upper portion of the elongate bar, a tibial support configured to at least partially encompass an anterior portion of a tibia of a user.

In embodiments of the invention, the device optionally includes a foot support that is sized to fit into corresponding footwear of the user drop foot.

In embodiments of the invention, the device optionally includes an elongate member that is mechanically coupled to the foot support. The elongate member optionally has a lower portion prolonging to an upper portion. The device optionally further includes a lower-leg-holder that is mechanically coupled to the elongate member. The lower-leg-holder optionally includes a support-brace that enables a corresponding shin to rest thereon.

In embodiments of the invention, the lower portion of the elongate member optionally extend from a heel portion of the foot support upwards and rearwards towards a corresponding lower leg's calf, wherein the upper portion optionally further extend forwardly in a direction corresponding to the lower leg's shin.

In embodiments of the invention, forward tilting of the lower leg against the support-brace causes the elongate member to bend forward in a direction corresponding to the user gait, wherein the forward bending causes the development of potential energy in the ankle foot orthosis device. At least some of the potential energy is optionally released during the toe-off phase of the gait cycle, thereby at least partially compensating for the energy lost due to the drop foot condition.

In embodiments of the invention, some of the potential energy is optionally released during gait phases subsequent to the toe-off phase.

In embodiments of the invention, the elongate member of the ankle foot orthosis device is optionally flexible.

In embodiments of the invention, the foot support of the ankle foot orthosis device is flexible.

In embodiments of the invention, the foot support optionally weighs, for example, approximately 70 grams, 60 grams, 50 grams, 40 grams or 30 grams.

In embodiments of the invention, the elongate member optionally weighs, for example, approximately 100 grams, 90 grams, 80 grams, 70 grams or 60 grams.

In embodiments of the invention, lower leg holder optionally weighs, for example, approximately 20 grams, 25 grams, 30 grams, 35 grams, 40 grams, 45 grams or 50 grams.

In embodiments of the invention, the device weighs approximately, for example, 500 grams, 400 grams, 350 grams and the like.

In embodiments of the invention, the foot support optionally includes at least one of the following first materials: carbon fibers, and graphite fibers.

In embodiments of the invention, the first material is optionally disposed within at least one of the following second materials: epoxy resin, polydicyclopentadiene, and polyimide.

In embodiments of the invention, the density and the structure of the first material and/or the second material optionally dictate the mechanical properties of the foot support.

In embodiments of the invention, the foot support is optionally ergonomically designed to substantially fit the natural contour of a sole of the drop foot of the user.

In embodiments of the invention, the foot support is optionally sized to fit easily, snugly and securely inside the user corresponding footwear.

In embodiments of the invention, the mechanical properties of the foot support is optionally engineered as to enable substantial fitting of the foot support with the natural contour of a sole of a user drop foot during all phases of the user gait cycle.

In embodiments of the invention, the elongate member is optionally integrally formed with the foot support.

In embodiments of the invention, the elongate member is optionally fixedly coupled to the foot support with at least one elongate-member-fastener.

In embodiments of the invention, the support-brace is optionally secured to some portion of the shin by straps.

In embodiments of the invention, the elongate member is optionally made out of at least one of the following materials: high carbon steel, and very high carbon steel. However, the elongate member retains spring characteristics, i.e., elongate member is flexible.

In embodiments of the invention at least some parts of the elongate member is optionally shaped and fixedly coupled to foot support via the at least one elongate-member-fastener such that elongate member is substantially aligned with the anatomic axis of ankle of the user drop foot.

In embodiments of the invention, the lower portion of the elongate member extends from a heel portion substantially in alignment with the drop foot's ankle in a direction corresponding to a posterior position with regard to the drop foot's heel bone and ankle, wherein the posterior position is optionally substantially above the heel bone and the ankle.

In embodiments of the invention, the at least one elongate-member-fastener and/or the elongate member and/or the foot support are replaceable.

In embodiments of the invention, the at least one elongate-member-fastener includes a connector comprising of a base that is optionally integrally formed with a protruding plate.

In embodiments of the invention, the protruding plate is optionally positioned adjacent to the inner side of drop foot, such to enable the fixedly coupling of the elongate member to the protruding plate by fastener means.

In embodiments of the invention, padding elements are optionally fitted onto the foot support to provide comfortable cushioning for the drop foot's sole.

The present invention further discloses a method of fabricating an ankle foot orthosis device for assisting a user having a drop foot.

In embodiments of the invention, the method optionally includes, for example, the act of fabricating a foot support having a heel portion by, for example, laying up several layers of composite material.

In embodiments of the invention, the method optionally includes, for example, the act of fabricating an elongate member that optionally have a lower and an upper portion that are bent relative to each other and wherein the upper portion is a prolongation of the lower portion.

In embodiments of the invention, the method optionally includes, for example, the act of fabricating a lower-leg-holder, which optionally includes a U-shaped support-brace having an inner surface.

In embodiments of the invention, the method optionally includes, for example, the act of mechanically coupling the elongate member to a heel portion of the foot support such that the lower portion extends rearwardly from the heel portion towards the drop foot's corresponding calf and such that the upper portion extends anteriorly towards the drop foot's corresponding shin.

In embodiments of the invention, the method optionally includes, for example, the act of mechanically coupling the lower-leg-holder to the elongate member such that a curved part of the support-brace substantially points in a direction that corresponds to the user direction of gait, thereby enabling the user to rest his/her lower leg that corresponds to the drop foot against the inner surface of the support-brace.

BRIEF DESCRIPTION OF THE DRAWINGS

The subject matter regarded as the invention will become more clearly understood in light of the ensuing description of embodiments thereof, given by way of example only, with reference to the accompanying Figures, wherein:

FIG. 4A is a schematic isometric illustration of a foot support of the ankle foot orthosis of FIG. 1, according to some embodiments of the invention;

FIG. 4B is a schematic cross-sectional side view of the foot support of the ankle foot orthosis of FIG. 1, according to some embodiments of the invention;

FIG. 20 is a detail of a frontal hinge of the side spring ankle foot orthosis of FIG. 11, according to some embodiments of the invention.

Figure 1:
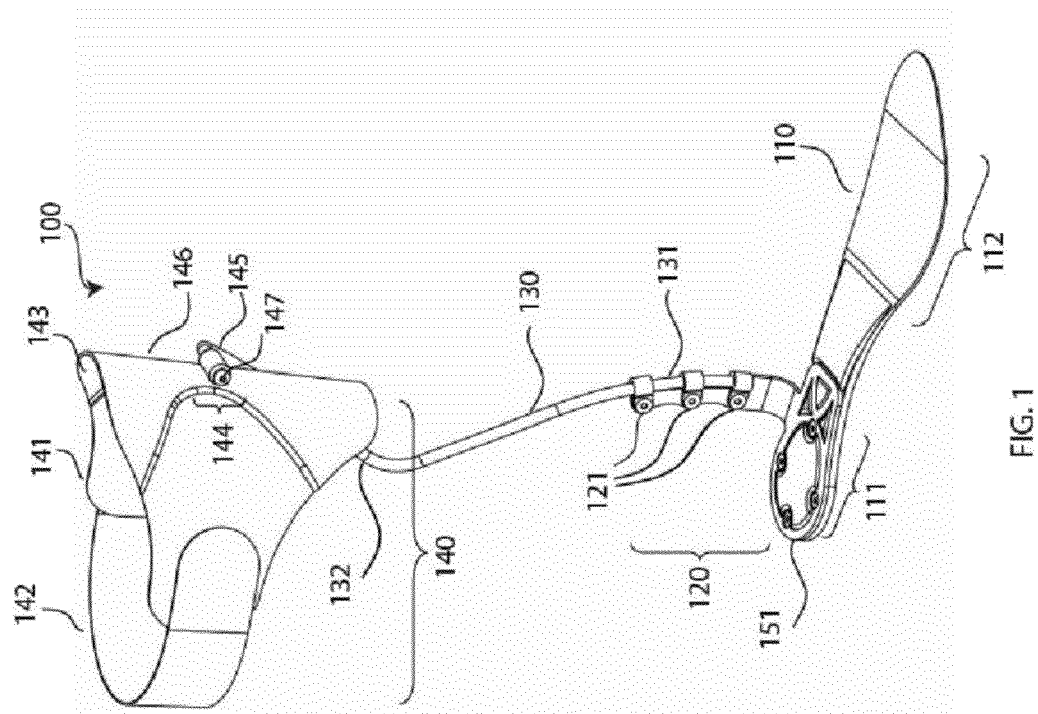
FIG. 1 is a schematic isometric assembly view of an ankle foot orthosis device, according to some embodiments of the invention.

The drawings taken with description make apparent to those skilled in the art how the invention is may be embodied in practice.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate identical elements.

DESCRIPTION OF THE INVENTION

The present invention, in some embodiments thereof, relates to orthoses and, more particularly, but not exclusively, to an ankle foot orthosis.

According to some embodiments of the invention, the AFO includes a flexible foot support to which a flexible elongate member is substantially fixedly coupled. The AFO further includes a lower-leg-holder that is mechanically coupled to an upper part of the elongate member. The AFO is designed in a manner such that when it is suitably engaged with a user drop foot, the AFO stores potential energy during, for example, the transition from the mid-stance to the terminal-stance phase of the user gait cycle. At least some of the stored potential energy is optionally released during the subsequent toe-off phase of the user gait cycle, whereby the released potential energy may at least partially compensate for, e.g., the muscle weakness in the drop foot. Consequently, the AFO optionally causes ground clearance of the user drop foot during at least some of the gait cycle's swing phases.

Additionally, in embodiments including a side spring, the side spring aids in storing energy associated with forward motion dorsiflexion of the foot. Furthermore, the AFO embodiment with the side spring facilitates pronation and supination associated with the gait cycle which is passive in a drop foot condition. Furthermore, the side spring aids in storing the energy associated with forward motion dorsiflexion of the foot.

An embodiment is an example or implementation of the invention. The various appearances of "one embodiment," "an embodiment" or "some embodiments" do not necessarily all refer to the same embodiments.

Although various features of the invention may be described in the context of a single embodiment, the features may be provided separately or in any suitable combination. Conversely, although the invention may be described herein in the context of separate embodiments for clarity, the invention may be implemented in a single embodiment.

Reference in the specification to "one embodiment", "an embodiment", "some embodiments" or "other embodiments" means that a particular feature, structure, or characteristic described in connection with the embodiments is included in at least one embodiment, but not necessarily all embodiments, of the invention.

It is understood that the phraseology and terminology employed herein is not to be construed as limiting, and is for descriptive purpose only.

The principles and uses of the teachings of the present invention may be better understood with reference to the accompanying description, figures and examples.

It should be understood that the details set forth herein do not construe a limitation to an application of the invention. Furthermore, it should be understood that the invention can be carried out or practiced in various ways and that the invention can be implemented in embodiments other than the ones outlined in the description below.

It should be understood that the terms "including", "comprising", "consisting" and grammatical variants thereof do not preclude the addition of one or more components, features, steps, integers or groups thereof and that the terms are not to be construed as specifying components, features, steps or integers.

If the specification or claims refer to "an additional" element, that does not preclude there being more than one of the additional element.

It should be understood that where the claims or specification refer to "a" or "an" element, such reference is not to be construed as there being only one of that element.

It should be understood that where the specification states that a component, feature, structure, or characteristic "may", "might", "can" or "could" be included, that particular component, feature, structure, or characteristic is not required to be included.

The descriptions, examples, methods and materials presented in the claims and the specification are not to be construed as limiting but rather as illustrative only.

Meanings of technical and scientific terms used herein are to be commonly understood as by one of ordinary skill in the art to which the invention belongs, unless otherwise defined.

The present invention can be implemented in the testing or practice with methods and materials equivalent or similar to those described herein.

Any publications, including patents, patent applications and articles, referenced or mentioned in this specification are herein incorporated in their entirety into the specification, to the same extent as if each individual publication was specifically and individually indicated to be incorporated herein. In addition, citation or identification of any reference in the description of some embodiments of the invention shall not be construed as an admission that such reference is available as prior art to the present invention.

The terms "bottom", "below", "top" and "above" and the like that may be specified herein do not necessarily indicate that a "bottom" component is below a "top" component, or that a component that is "below" is indeed "below" another component or that a component that is "above" is indeed "above" another component as such directions, components or both may be flipped, rotated, moved in space, placed in a diagonal orientation or position, placed horizontally or vertically, or similarly modified. Accordingly, it will be appreciated that the terms "bottom", "below", "top" and "above" may be used herein for exemplary purposes only, to illustrate the relative positioning or placement of certain components, to indicate a first and a second component, or to do both, such as when viewing them in the figures.

It should be understood that, unless otherwise indicated, the term "couple", "coupled", "coupling", and grammatical variations thereof as used herein, refers to the mechanical coupling between a plurality of elements, wherein the mechanical coupling between the plurality of elements may refer to an embodiment in which the different elements are substantially fixedly coupled to each other, as well as to another embodiment in which the plurality of elements may be integrally formed with each other.

Where applicable, although state diagrams, flow diagrams or both may be used to describe embodiments, the invention is not limited to those diagrams or to the corresponding descriptions. For example, flow need not move through each illustrated box or state, or in exactly the same order as illustrated and described.

Figure 2:
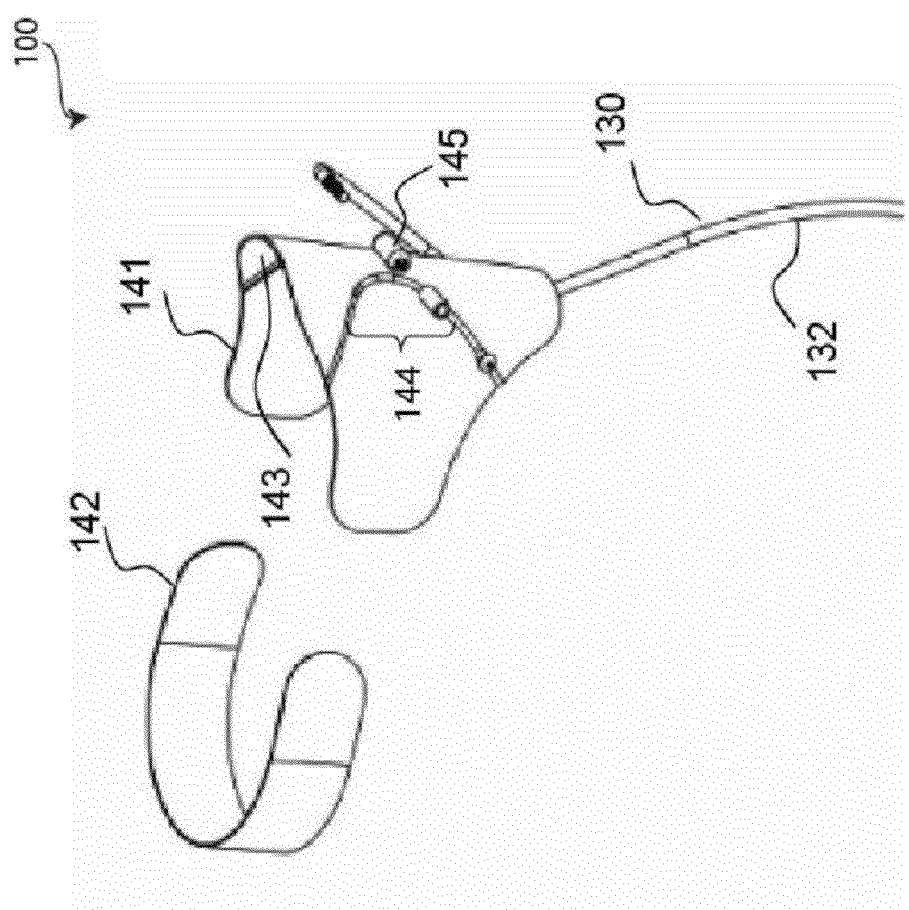
FIG. 2 is a schematic isometric exploded view of the elongate member and lower-leg-holder of the ankle foot orthosis of FIG. 1, according to some embodiments of the invention.
Figure 3:
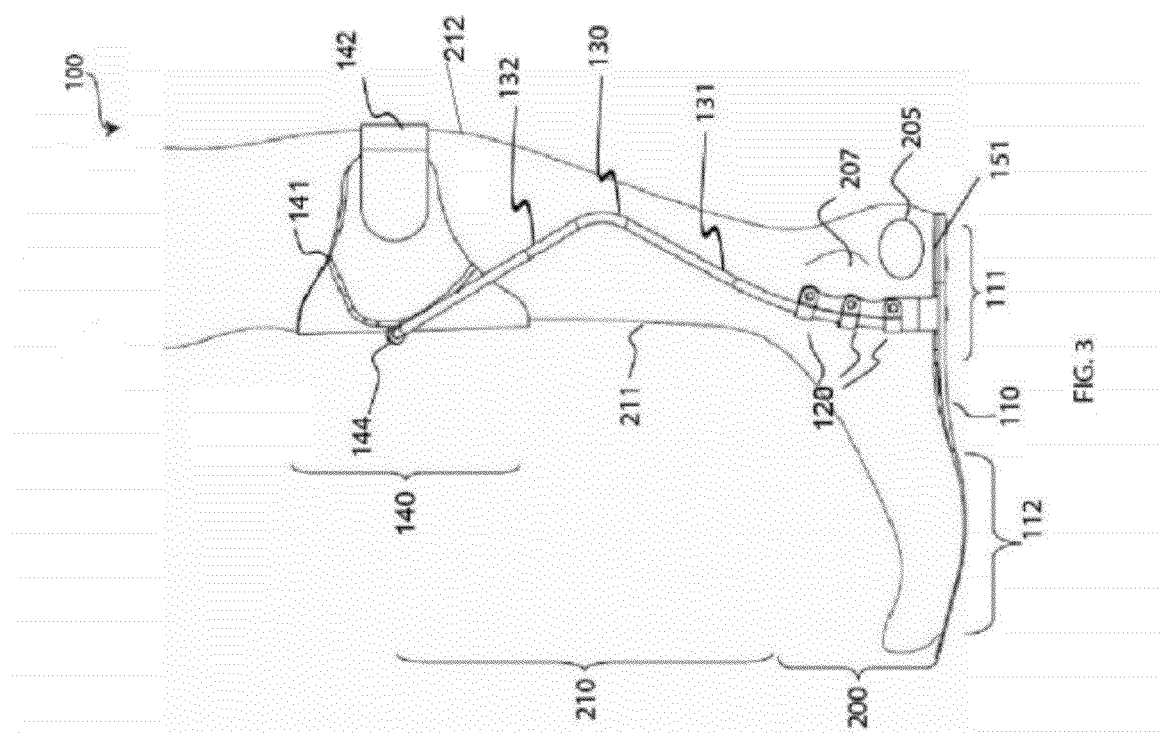
FIG. 3 is a schematic side view of the ankle foot orthosis device of FIG. 1, adjusted to a user drop foot, according to some embodiments of the invention.
Figure 5:
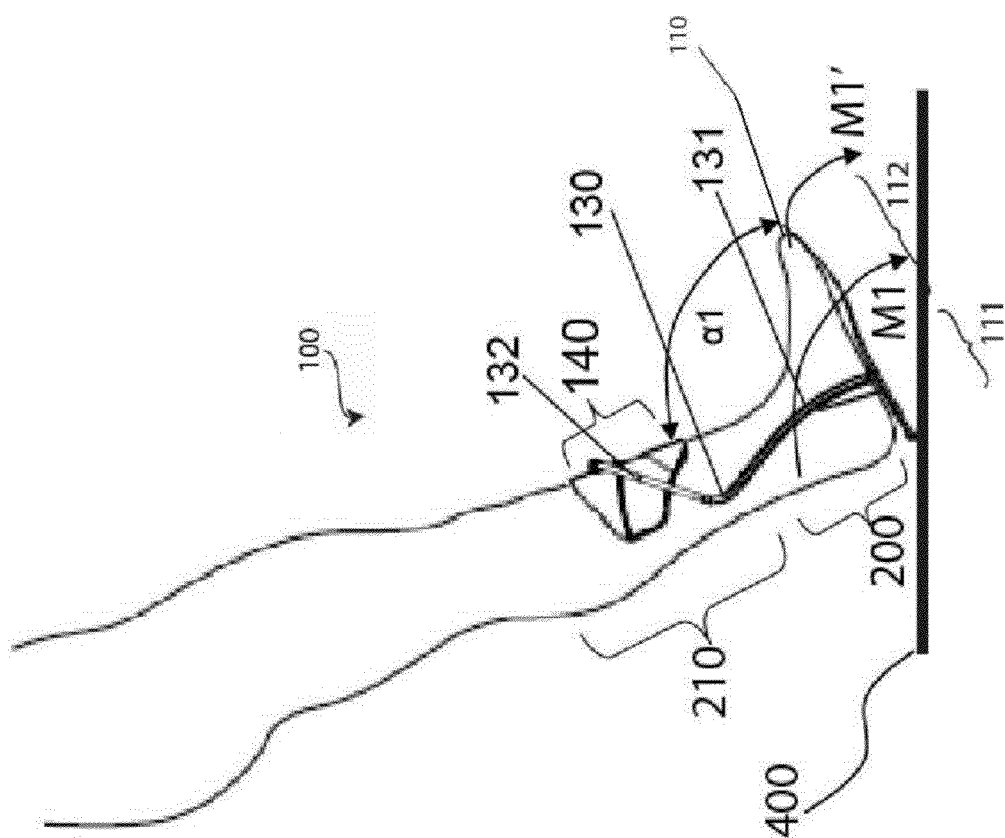
FIGS. 5-8 are schematic illustrations of a gait cycle during use of the ankle foot orthosis of FIG. 1, according to some embodiments of the invention.
Figure 6:
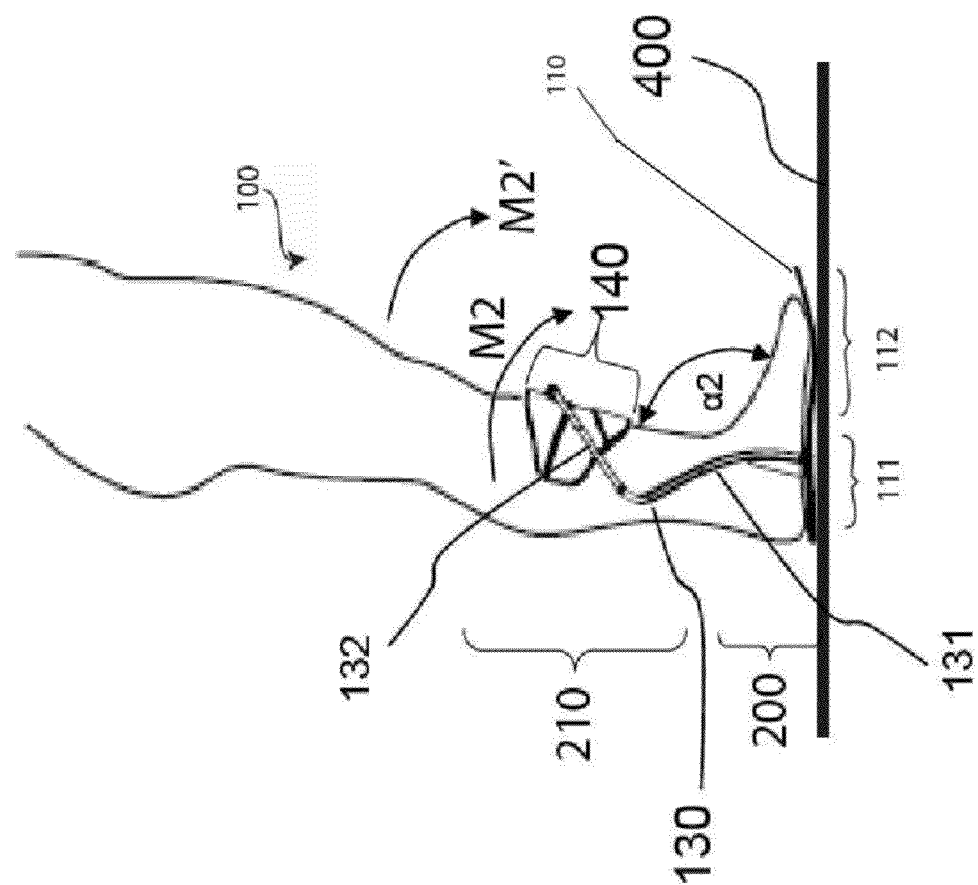

With respect to the drawings, reference is now made to FIGS. 1-3: According to some embodiments of the invention, an AFO 100 is designed to provide a user drop foot 200 with stability and assistance to aid in duplicating normal gait pattern.

According to some embodiments of the invention, AFO 100 includes an ergonomically designed foot support 110 that is sized to fit easily, snugly and securely inside a user footwear (not shown); such as footwear being, for example, a shoe, a sandal, or a boot.

In addition, AFO 100 is designed to enable comfortable pulling out of the user foot from the user footwear. Furthermore, the ergonomics and/or the mechanical properties of foot support 110 is optionally designed and/or engineered, respectively, to enable substantial fitting of foot support 110 with the natural contour of a sole of user drop foot 200 during all phases of the user gait cycle.

Referring now to FIGS. 4A and 4B, the mechanical properties and/or the ergonomics of foot support 110 is optionally engineered, for example, by suitably structuring the materials out of which the foot support 110 is made, such that foot support 110 assists in compensating the user drop foot condition, which is optionally neurological and/or muscular and/or anatomic in origin.

The material(s) out of which foot support 110 is made is optionally lightweight and strong, as well as flexible. Foot support 110 optionally weighs, for example, less than 2 kilograms.

Foot support 110 is optionally made out of a composite material, e.g., as known in the art, or of any other suitable material. For example, foot support 110 optionally comprises a plurality of layers including a first material disposed within a second material, the first and the second materials making up a composite material, e.g., as known in the art. For example, the first material optionally comprises a plurality of layers of fiber (e.g., carbon fibers, graphite fibers).

The fiber layers are optionally embedded within the second material that optionally comprises a thermoset such as, for example, epoxy resin, polydicyclopentadiene, polyimide or any other suitable material.

According to some embodiments of the invention, the second material is optionally disposed relative to the first material of as to form a matrix-like structure, e.g., as known in the art, wherein the second material optionally serves as a bond material holding the first material together. Various parameters of the first and/or the second material such as, for example, orientation, thickness, density or other parameters optionally influence or dictate the mechanical properties of the composite material.

For example, higher the density of the fibers within a layer or a certain portion of the layer, may contribute to the rigidity of the layer or portion of the layer. This effect is, for exemplary purposes only, schematically illustrated in FIG. 4B, wherein a heel portion 111 of foot support 110 includes more layers of fibers 115 than a ball portion 112. Consequently, heel portion 111 is optionally less flexible to bending than ball portion 112, as is schematically illustrated by the more extensive bending of ball portion 112 compared to the bending of heel portion 111.

According to some embodiments of the invention, foot support 110 is optionally made of additional or alternative materials such as, for example; fiber reinforced polymers (e.g., carbon-fiber reinforced plastic, glass-fiber reinforced plastic); thermoplastic composite material; thermoplastic composites or any other suitable material(s).

In some embodiments of the invention heel portion 111 is superimposed on foot support 110 and foot support includes flexible ball portion 112. As will be explained below, super imposition of heel plate 151 serves to create a leaf spring that brings the foot of the user back to 90° with respect to the leg.

Referring back to FIGS. 1-3, to use AFO 100, the user places foot support 110 inside the footwear (not shown) that corresponds to the body side of the user drop foot 200. For example, if drop foot 200 is the user left foot, the user adjusts foot support 110 to a left-sided footwear.

The user then inserts his/her drop foot 200 into the corresponding footwear which he/she optionally dons substantially in the same manner as regular footwear on an unaffected foot. Once the foot support 110 and drop foot 200 are in place, the user optionally secures AFO 100 to his/her lower leg 210 by means of a lower-leg-holder 140, as will be described hereinbelow.

According to some embodiments of the invention, a vertical bar 130 is coupled to heel portion 111 of foot support 110 by means of a coupler 120, which is optionally substantially semi-rigid. A number of elongate-member-fasteners 121 are described hereinbelow, with respect to FIG. 9. According to some other embodiments of the invention, vertical bar 130 is optionally integrally formed with heel portion 111 of foot support 110. Vertical bar 130 is flexible as will be described below.

In some embodiments vertical bar 130 comprises two portions; a lower portion 131 and an upper portion 132. Lower portion 131 optionally extends rearwardly from heel portion 111 towards a calf 212, and upper portion 132 optionally extends anteriorly towards a shin 211. Accordingly, lower portion 131 is optionally bent relative to upper portion 132.

Furthermore, according to some embodiments of the invention, at least some parts of elongate member are optionally shaped and fixedly coupled to foot support 110 via elongate-member-fasteners 121 such that vertical bar 130 substantially intersects the anatomic axis of an ankle 207.

More specifically, lower portion 131 optionally extends from heel portion 111 in alignment with ankle 207 towards a posterior position with regard to a calcaneus 205 and ankle 207, wherein the flexible portion of vertical bar 130 is optionally above ankle 207.

Consequently, AFO 100 is designed and adjustable to drop foot 200 as to possibly enable substantial imitation of the biomechanics of a healthy foot. Due to the alignment of vertical bar 130 with ankle 207 and calcaneus 205, AFO 100 may facilitate the movement of foot 200 in proper anatomic function.

According to some embodiments of the invention, vertical bar 130 is optionally made out of, for example, a resilient steel material such as, for example, high carbon steel, very high carbon steel or any other suitable material.

According to some embodiments of the invention, lower-leg-holder 140 optionally includes a U-shaped support-brace 141 that is optionally mechanically coupled, e.g., via an outer front part 146, to the end part of vertical bar 130 by leg-holder-fasteners 144 such that a curved part of U-shaped support-brace 141 substantially points in a direction that corresponds to the user gait.

Leg-holder-fastener(s) 144 comprises, for example, a sleeve 145 that is fixedly coupled to outer front part 146 and into which the end part is tightly fitted. According to some embodiments of the invention, lower-leg-holder 140 optionally further include a securing end 147 (FIG. 1) such as, for example, a rivet, for preventing the sliding out of the end part from sleeve 145.

According to some embodiments of the invention, lower-leg-holder 140 is optionally shaped to substantially fit onto at least some part of shin 211, such that lower leg 210 can rest against an inner surface 143 of U-shaped support-brace 141. Furthermore, according to some embodiments of the invention, AFO 100 is secured to user lower leg 210 by, for example, straps 142.

FIGS. 5-8 demonstrate AFO 100 assisting the user in overcoming the effects of the drop foot condition such that the user can walk while duplicating some of the biomechanics of normal gait; normal gait referring to the gait exhibited by the limbs of a person unaffected with a drop foot condition.

It should be understood that angles $\alpha_1$, $\alpha_2$, $\alpha_3$, $\alpha_4$, as specified herein are not to be referred to as being angles of fixed size but rather as angles during the initial-contact, mid-stance, terminal-stance and toe-off phase of the gait cycle, respectively, wherein each of the angles optionally dynamically change during each of the phases.

During the initial-contact phase (FIG. 5), at least some of heel portion 111 of foot support 110 engages with floor 400. The engagement of heel portion 111 with floor 400 causes drop foot 200 to apply a moment M1 on foot support 110 around coupler 120 such that a tip 131 of drop foot 200 optionally pivots away from lower leg 210, as schematically indicated with arrow M1'. During the initial-contact phase, angle $\alpha_1$ between tip 131 of drop foot 200 and shin 211 is optionally slightly larger than approximately 90°. For example, during initial-contact phase, angle $\alpha_1$ may optionally have values of for example, approximately 93°, 95° and 97°. Angle $\alpha_1$ optionally has other values during the initial-contact phase.

Upon completion of the initial-contact phase (FIG. 5), the user transitions to the mid-stance phase (FIG. 6), wherein in the mid-stance phase, both heel portion 111 and ball portion 112 are engaged with floor 400. During the mid-stance phase, lower leg 210 optionally rests against lower-leg-holder 140, thereby applying a moment M2 against inner surface 143 of support-brace 141 of lower-leg-holder 140. As lower leg 210 moves towards drop foot 200, as schematically indicated with arrow M2', angle $\alpha_2$ between tip 131 of foot 200 and shin 211 decreases with respect to angle $\alpha_1$ to by, for example, approximately 2°-5°, such that $\alpha_2$ optionally attain a value of, for example, approximately 90° or approximately 88°. Angle $\alpha_2$ optionally has other values during the mid-stance phase.

Figure 7:
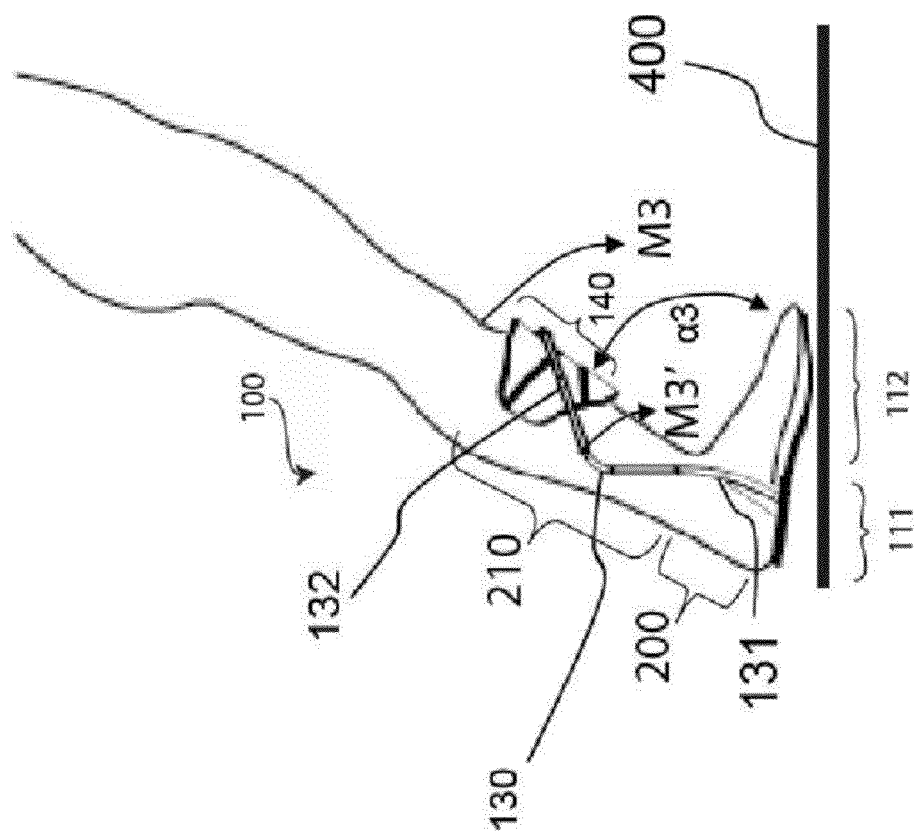
Figure 8:
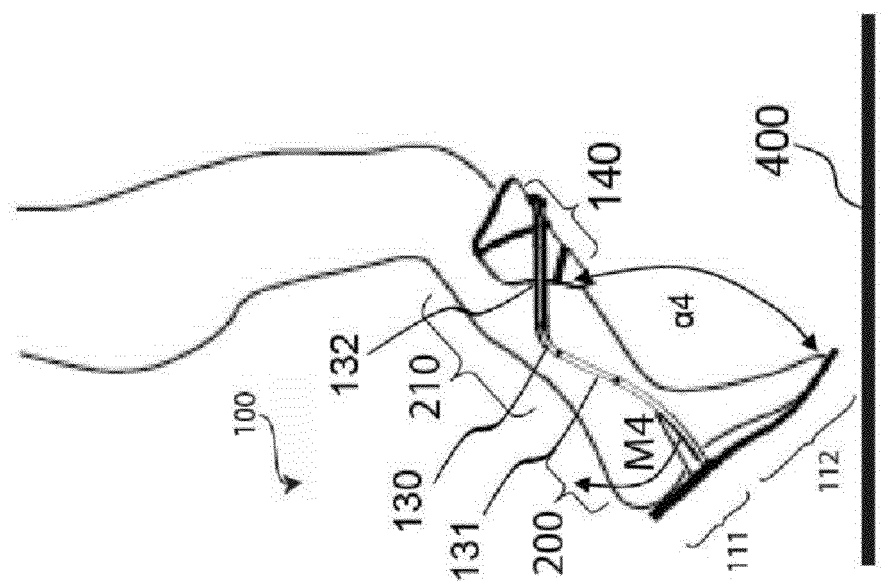

Upon completion of the mid-stance phase (FIG. 6), the user transitions to the terminal-stance phase of gait (FIG. 7), wherein in the terminal-stance phase, heel portion 111 disengages from floor 400 due to the force and/or moment applied by lower leg 210 against inner surface 143 of U-shaped support-brace 141. During the terminal-stance phase (FIG. 7), angle $\alpha_3$ between tip 131 of foot 200 and shin 211 optionally further decrease with respect to angle $\alpha_2$ up to, for example, approximately 85°. Angle $\alpha_3$ optionally has other values during the terminal-stance phase (FIG. 7).

It should be understood that AFO 100 is adjustable to meet individual user needs. For example, AFO 100 is individually adjustable to a user anatomy and biomechanical behavior. Accordingly, AFO 100 is optionally adjusted such that during the terminal stance phase (FIG. 7) of a first user, angle $\alpha_3$ optionally decrease up to approximately 83°, whereas during the terminal stance phase of a second user, angle $\alpha_3$ optionally decrease only up to approximately 85°.

In order to perform a transition from the mid-stance phase (FIG. 6) to the terminal-stance phase (FIG. 7), the user typically shifts his/her body weight to the gait's direction and towards the side of drop foot 200, while tilting lower leg 210 downwards and forwards against inner surface 143 of support-brace 141. Shifting his/her body weight forward in a direction that corresponds to the user gait, optionally result in a moment M3 on inner surface 143 of support-brace 141. Since vertical bar 130 has flexibility, moment M3 causes vertical bar 130 to flex in a direction that is schematically indicated with arrow M3'. Concurrent to the flexing of vertical bar 130, drop foot 200 optionally pivot towards lower leg 210 to take up for the shortening of the distance between the extremities of vertical bar 130 occurring due to the bending thereof.

In consequence, vertical bar 130 develops therein some potential energy of which some is optionally released during the subsequent toe-off phase (FIG. 8) in form of, e.g., moment M4 or other moments and/or forces. During the toe-off phase, both heel portion 111 and ball portion 112 disengage from floor 400. The lower part of vertical bar 130 optionally exert, for example, moment M4 on heel portion 111 of foot support 110.

Moment M4 and/or other forces and/or moments optionally help compensating for the force lost due to, e.g., muscle weakness in drop foot 200 and thereof assists the user in performing the toe-off phase without dragging drop foot 200 along floor 400. Correspondingly, AFO 100 optionally causes ground clearance of user drop foot 200 during the toe-off phase and during at least some of the subsequent swing phases.

Figure 9:
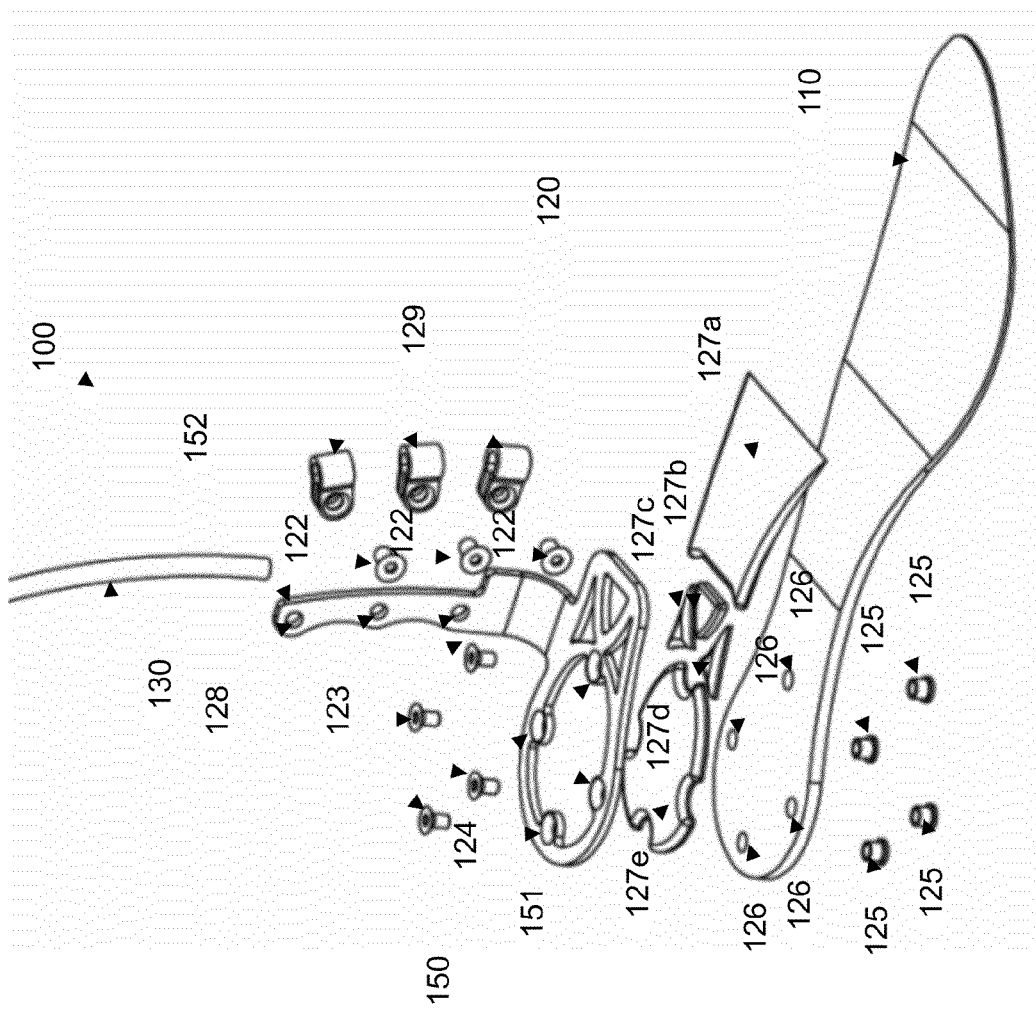
FIG. 9 is an exploded view of the lower portion of the ankle foot orthosis of FIG. 1, according to some embodiments of the invention.

Further reference is now made to FIG. 9. According to some embodiments of the invention, coupler 120 optionally includes a connector 150 that optionally includes a base 151 that is optionally integrally formed with a protruding plate 152. Plate 152 is optionally positioned adjacent to the inner side of drop foot 200. According to some embodiments of the invention, plate 152 is optionally adapted to fixedly couple thereto vertical bar 130 by means of, e.g., clamps 129, which optionally clamp vertical bar 130 therein. According to some embodiments of the invention, vertical bar 130 optionally has holes 128 suitable for receiving clamp securing fasteners 122. Clamp securing fasteners 122 are optionally used for securing clamps 129 onto vertical bar 130. Securing fasteners 122 are optionally, for example, bolts, nuts, rivets, and/or any other suitable fasteners.

According to some embodiments of the invention, base 151 is optionally fixedly coupled to heel portion 111 of foot support 110 via, e.g., heel fasteners 123, comprising, for example, bolts, nuts, rivets and the like. According to some embodiments of the invention, base 151 and heel portion 111 optionally receive heel fasteners 123 via holes 124 and 126, respectively. The position of heel fasteners 123 is optionally secured by securing means 125, comprising, for example, suitable stoppers.

In some embodiments of the invention, padding elements 127a, 127b, 127c, 127d and 127e are optionally fitted onto foot support 110 in a manner that substantially complements the shape of base 151, thereby providing comfortable cushioning to the sole of drop foot 200.

According to some embodiments of the invention, all of the abovementioned elements of AFO 100 are optionally replaceable.

In embodiments of the invention, foot support 110 optionally weighs, for example, approximately 70 grams, 60 grams, 50 grams, 40 grams or 30 grams.

In embodiments of the invention, vertical bar 130 optionally weighs, for example, approximately 100 grams, 90 grams, 80 grams, 70 grams or 60 grams.

In embodiments of the invention, lower leg holder 140 optionally weighs, for example, approximately 20 grams, 25 grams, 30 grams, 35 grams, 40 grams, 45 grams or 50 grams.

In embodiments of the invention, AFO 100 weighs, for example, approximately 500 grams, 400 grams, 350 grams and the like.

Figure 10:
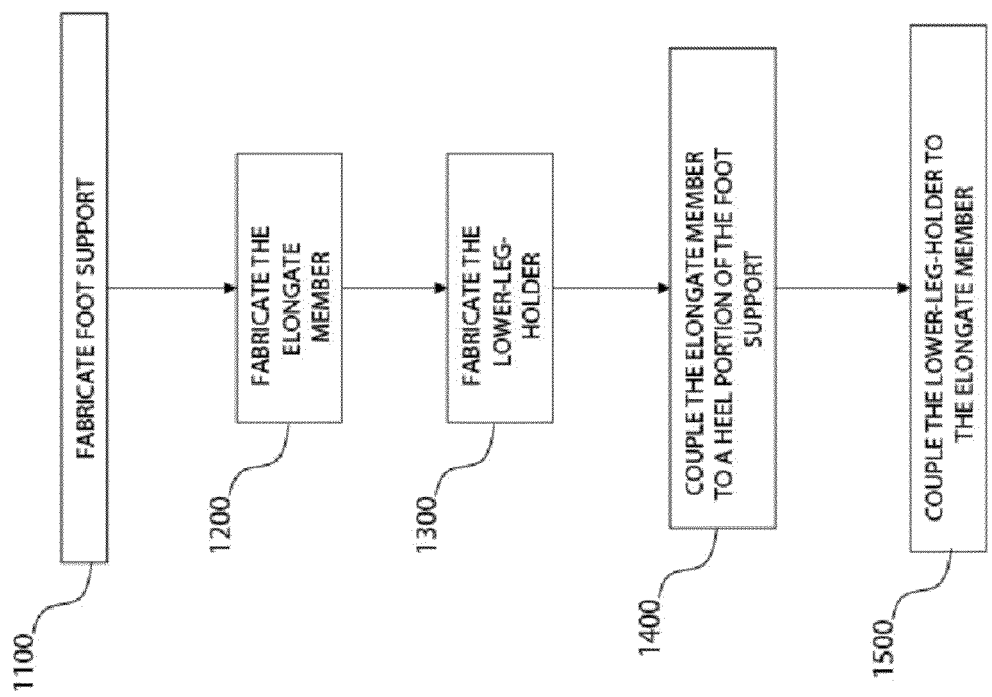
FIG. 10 is schematic flow-chart illustration of a method for fabricating the ankle foot orthosis device, according to some embodiments of the invention.

Reference is now made to FIG. 10. According to some embodiments of the invention, as indicated in stage 1100, a method for fabricating an ankle foot orthosis device, optionally includes, for example, the act of fabricating foot support 110 by, for example, laying up several layers of, e.g., composite material.

According to some embodiments of the invention, at a stage 1200, the method optionally includes, for example, the act of fabricating vertical bar 130.

According to some embodiments of the invention, at a stage 1300, the method optionally includes, for example, the act of fabricating lower-leg-holder 140.

According to some embodiments of the invention, at a stage 1400, the method optionally include, for example, the act of mechanically coupling vertical bar 130 to heel portion 111 of foot support 110.

This is optionally accomplished in a manner such that lower portion 131 extends rearwardly from heel portion 111 towards drop foot's 200 corresponding calf 212 and such that upper portion 132 extends anteriorly towards the drop foot's 200 corresponding shin 211.

According to some embodiments of the invention, at a stage 1500, the method optionally includes, for example, the act of mechanically coupling lower-leg-holder 140 to vertical bar 130.

This is optionally accomplished in a manner such that such that the curved part of support-brace 141 substantially points in a direction that corresponds to the user direction of gait, thereby enabling the user to rest his/her lower leg 210 that corresponds to the drop foot 200 against inner surface 143 of support-brace 141.

Figure 11:
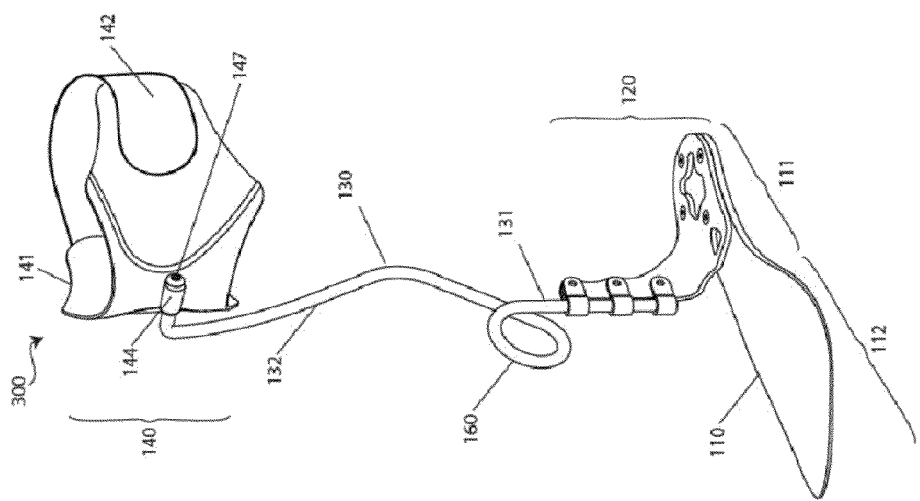
FIG. 11 is an assembly view of a side spring ankle foot orthosis device, according to some embodiments of the invention.

FIG. 11 shows a spiral spring AFO 300 in which elongated bar 130 includes a spiral spring 160 which creates flexibility between upper portion 132 and lower portion 131 in which heel portion 111 is superimposed on foot support 110.

Figure 12:
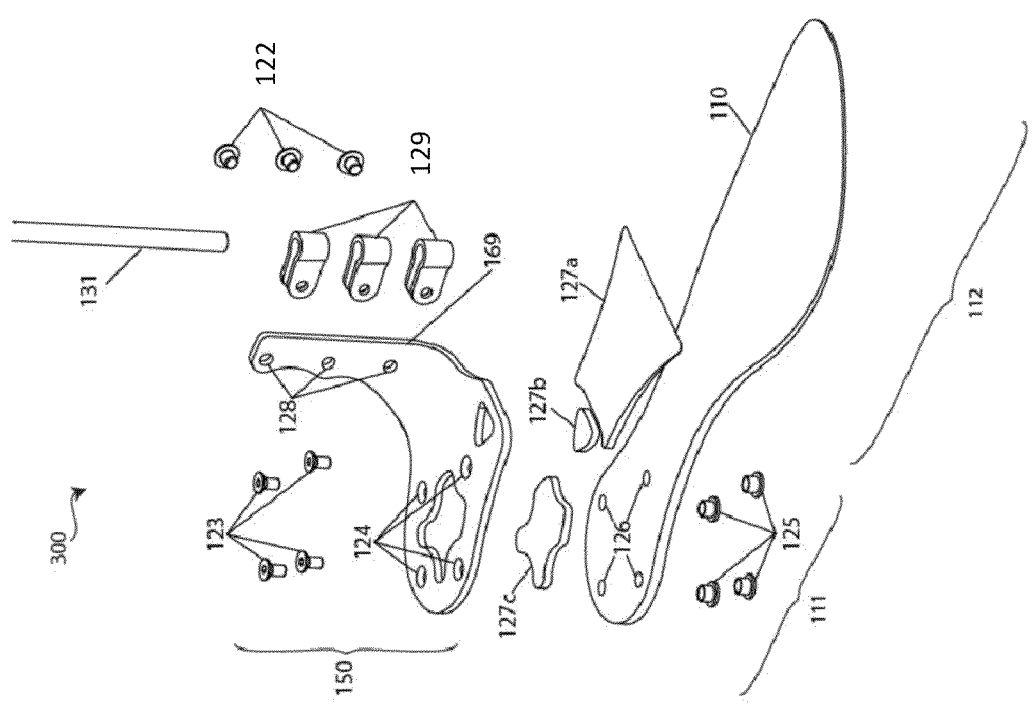
FIG. 12 is an exploded view of the side spring ankle foot orthosis of FIG. 11, according to some embodiments of the invention.

FIG. 12 shows embodiment 300 in which (compared to FIG. 9) heel portion 150 is attached to foot support 110 with sections 127a, b and c. Heel portion 150 comprises a main support 169 adapted to be fixedly coupled to vertical bar 130

Figure 13:
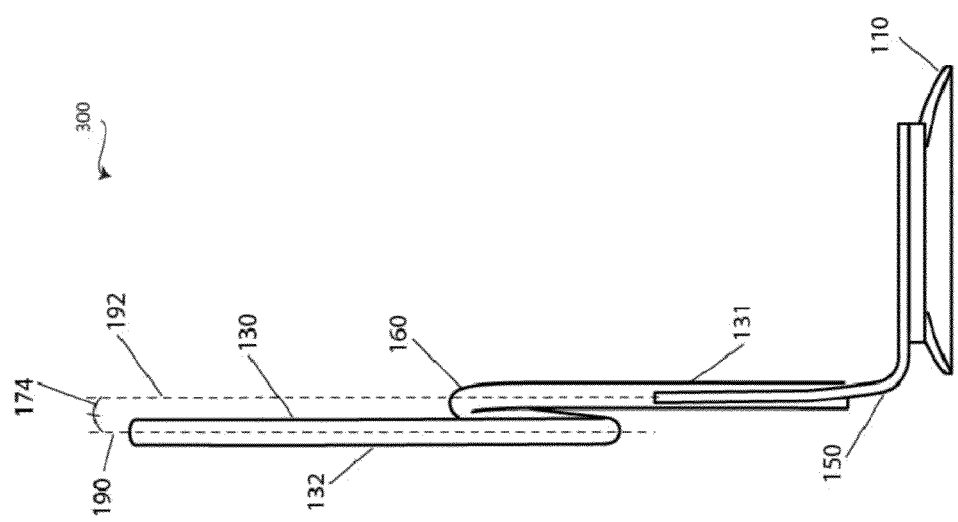
FIGS. 13-15 are frontal views of the side spring ankle foot orthosis of FIG. 11 during gait, according to some embodiments of the invention.
Figure 14:
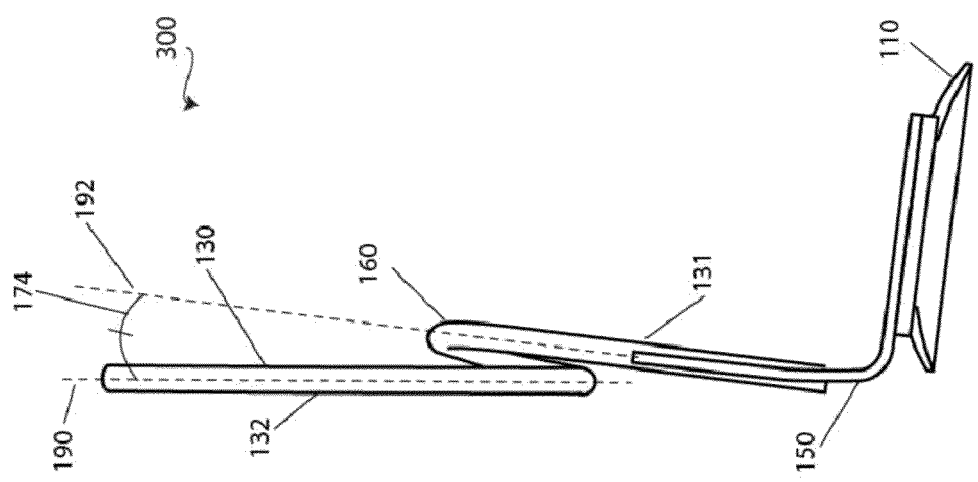
Figure 15:
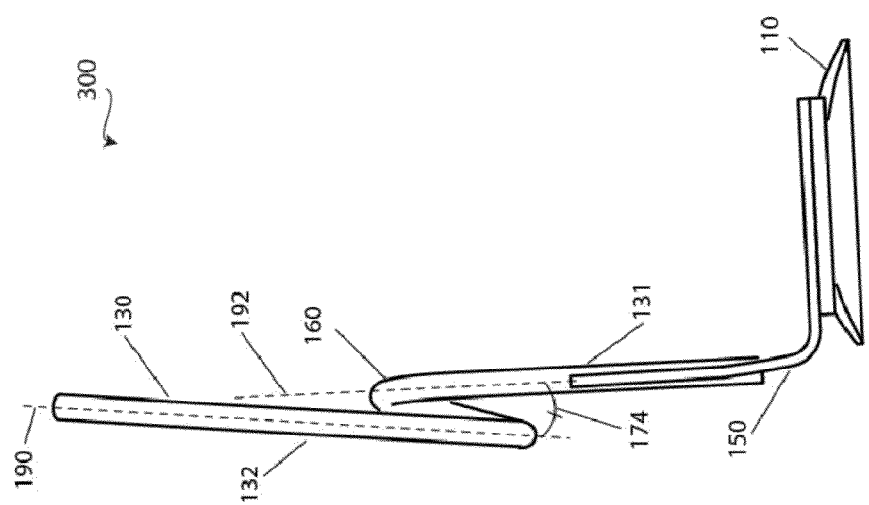

FIGS. 13-15 demonstrate that spiral spring 160 allows pronation and supination to be distributed between foot support 110 and vertical bar 130.

As seen in FIG. 13 during swing phase an angle 174 is parallel between an axis 190 and an axis 192 which go through upper portion 132 and lower portion 131 respectively.

As seen in FIG. 14, during heel strike and foot flat faces of gait, spiral spring 160 allows pronation such that angle 174 increases allowing footplate 110 pronate. Pronation is a portion of normal gait cycle in which the foot is substantially flexible and allows the foot to adapt to the terrain underneath.

Upon toe-off, as seen in FIG. 15, angle 174 decreases such that heel plates 110 assumes a supination position. The position of supination allows the foot to become a rigid lever which aids in the toe off cycle of gait. Spiral spring 160 allows this supination to occur and is offset from the user leg.

The inventor has discovered that providing spiral spring 160 not only allows pronation and supination of the foot, but allows this to occur without undue chaffing of the calf of the foot, because spring 160 is offset from the foot and tibia.

Referring to FIGS. 16-19, spring 160 is shown to aid in the propulsive phases of gait such that the spring between portion 111 and 112 is aided and assisted by spring 160.

Figure 16:
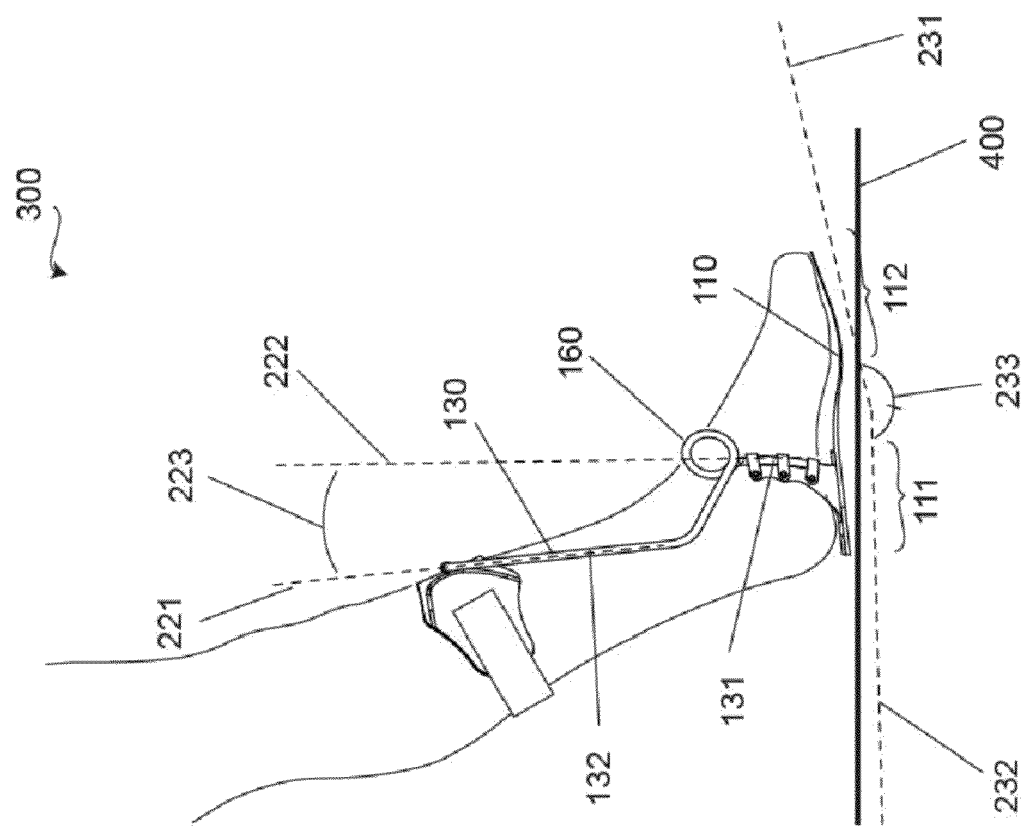
FIGS. 16-19 are side views of the side spring ankle foot orthosis of FIG. 11 during gait, according to some embodiments of the invention.

As seen in FIG. 16, foot support 110 is parallel to ground 400 and an angle 223 which represents the angle between axis 221 of upper portion 132 and 220 of lower portion 131, is above 90°.

Figure 17:
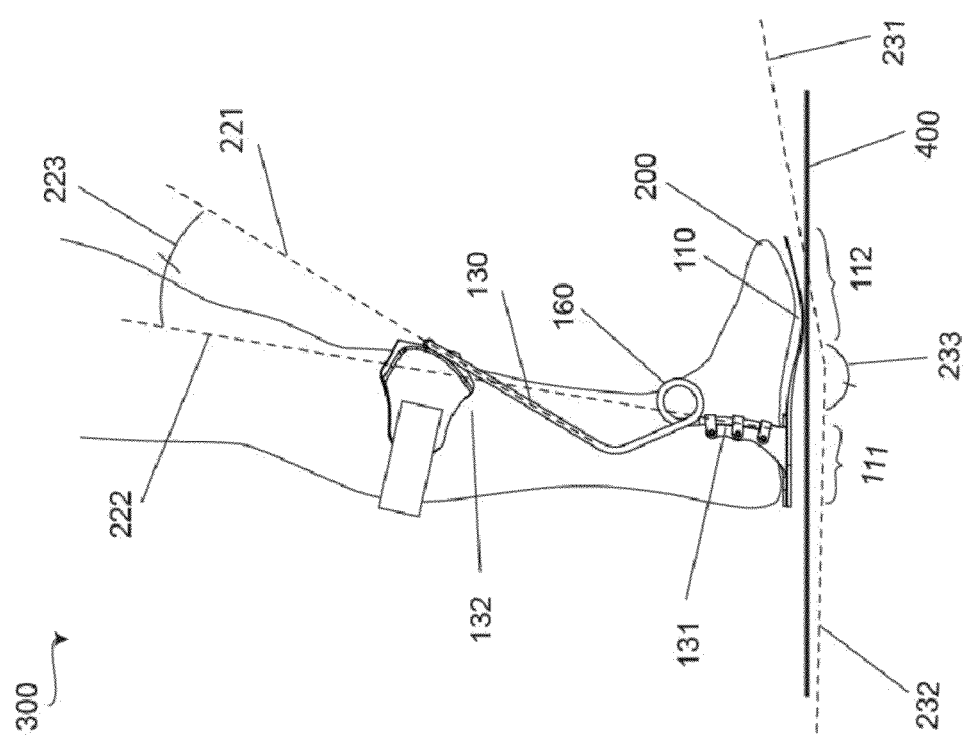

In FIG. 17 as the leg passes through foot flat, angle 223 becomes acute thereby reflecting the fact that spiral spring 160 has been put in tension that will later aid foot 200 in toe off.

Figure 18:
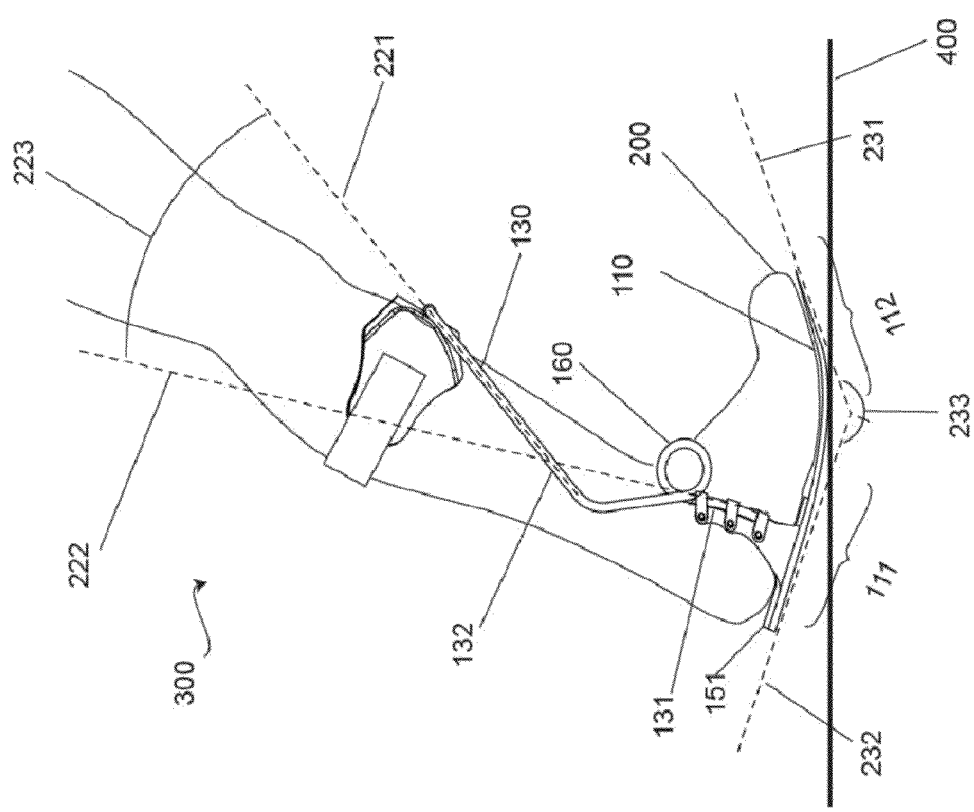

As seen in FIG. 18, in addition to acute angle 223, foot support 110 has assumed that angle between axes 232 and 231 consisting of an angle 233. As result forces are stored in both spiral spring 160 and footplate 110. This creates a propulsion for the user and also allows foot 200 to clear the ground without tripping, as seen in FIG. 19.

Figure 19:
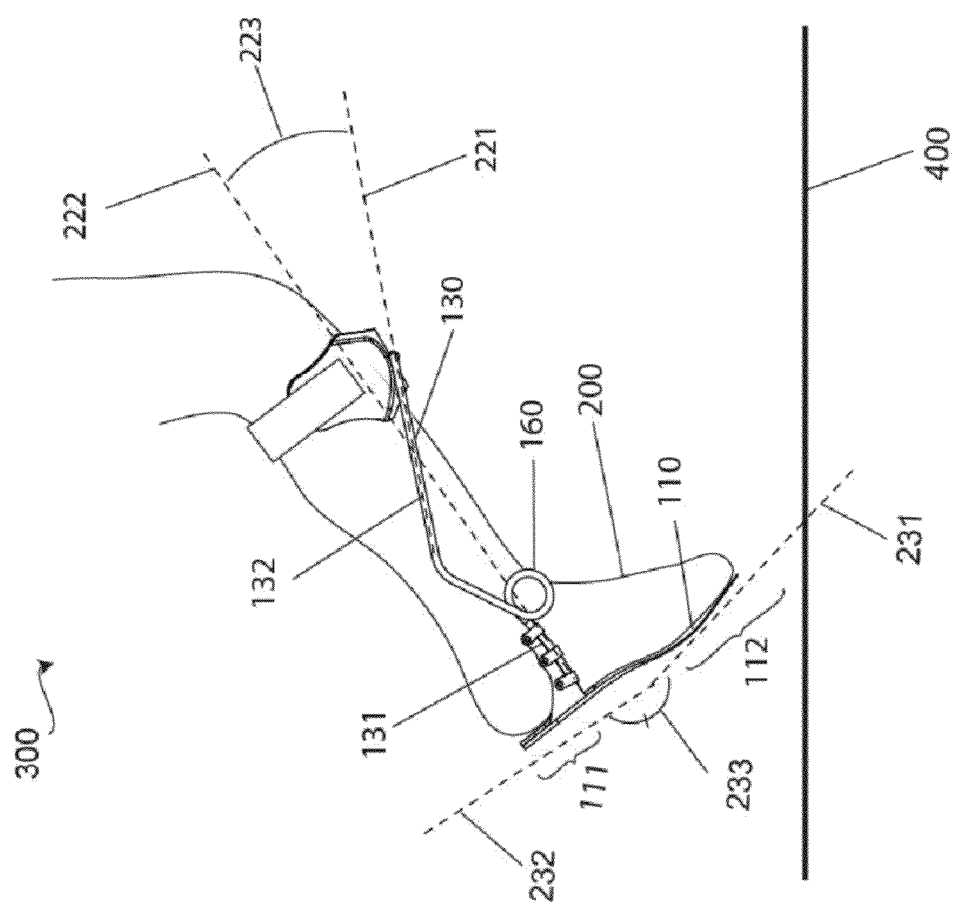

FIG. 19 shows that the energy in both angle 233 within foot support 110 and angle 223 controlled by spiral spring 160 have been released to ensure that foot 200 returns to a neutral position, thereby allowing foot 200 to effectively clear ground surface 400.

The inventor has discovered that by superimposing heel plate 151 on top of foot support 110, that during toe off phase of gait the bending forces of foot support 110 are simply optimized toward the forefoot of the user such that ball portion 112 acts as a spring such that as the patient weight on foot support 110 changes, the energy stored is transferred from heel plate 151 toward ball portion 112. The superimposition of heel plate 151 serves to create a leaf spring effect that brings the foot of the user quickly back to 90° with respect to the leg. Additionally the force of the propulsive portion of gait is divided between foot support 110 and spring 160.

FIG. 20 demonstrates the movement between upper portion 132 and U-shaped support-brace 141 in which axis 231 allows movement of plus or minus 10° such that the propulsive phase of gait does not cause chafing of the anterior tibia.

The instant invention includes modular components that can be fit to a user that allow a variety of measurements to be incorporated in the AFO, including height of the brace, size of the foot support, and the size of the shin support. The modular components and measurements, seen in FIG. 21, are but a few of the many examples that can be incorporated in the instant invention.

While the invention has been described with respect to a limited number of embodiments, these should not be construed as limitations on the scope of the invention, but rather as exemplifications of some of the embodiments. Those skilled in the art will envision other possible variations, modifications, and programs that are also within the scope of the invention. Accordingly, the scope of the invention should not be limited by what has thus far been described, but by the appended claims and their legal equivalents. Therefore, it is to be understood that alternatives, modifications, and variations of the present invention are to be construed as being within the scope and spirit of the appended claims.

What is claimed is:

1. An ankle foot orthotic device for assisting gait, the device comprising:
   a. a foot support having a shape and size configured to the plantar aspect of a user's foot, said foot support having a forward portion and a rearward portion;
   b. a heel plate coupled to an upper surface of said rearward portion;
   c. an upper rod having a longitudinal axis and a lower end connected to an offset;
   d. a lower rod having:
      i. a longitudinal axis;
      ii. a lower end connected to said heel plate; and
      iii. an upward end connected to said offset
   wherein said offset comprises a curved member;
   wherein said curved member curves substantially around a sagittal plane with respect to said foot support.

2. The device according to claim 1, wherein said offset is configured to allow relative movement along a coronal plane with respect to said foot support during user weight bearing.

3. The device according to claim 1, wherein said offset is configured to allow relative movement along a sagittal plane with respect to said foot support during user weight bearing.

4. The device according to claim 1, including a cuff connected to an upper end of said upper rod, said cuff configured to press against at least a portion of an anterior tibia.

5. The device according to claim 4, wherein said cuff is rotatably connected by a rotatable hinge to an upper end of said upper rod.

6. The device according to claim 5, wherein said rotatable hinge is configured to allow a swinging motion in said cuff along a sagittal plane with respect to said longitudinal axis of said upper rod.

7. The device according to claim 5, wherein said foot plate comprises a flexible material.

8. The device according to claim 1, wherein said heel plate is substantially rigid such that when the rear end of said rigid heel plate rises with respect to said foot support, and said forward portion is planted on a support surface, bending of said rigid heel plate is transferred beyond the front boundary of said heel plate.

9. The device according to claim 8, wherein when said forward portion is no longer in contact with said support surface, energy of said bending is transferred such that a sagittal axis passing through said forward portion becomes substantially aligned with a sagittal axis passing through said rearward position.

10. An ankle foot orthotic device for assisting gait, the device comprising:
    a. a rigid heel plate having a shape and size configured to encompass at least a portion of the plantar aspect of a user heel, said heel plate having a lower surface;
    b. a rod extending upward from said rigid heel plate
    c. a cuff connected to an upper end of said rod, said cuff configured to press against at least a portion of an anterior tibia;
    d. a foot support having a shape and size configured to encompass at least a portion of the plantar aspect of a user foot, said foot support including:
       i. a forward flexible portion;
       ii. a rearward portion having an upper surface rigidly connected to said lower surface of said rigid heel plate, such that when a rear end of said heel plate rises with respect to a sagittal axis of said foot support, and the forward portion is planted on a support surface, energy of bending is transferred to said forward flexible portion.

11. The device according to claim 10, wherein said rod includes a spring offset configured to transfer forces generated between said rod and said foot support to said foot support.

12. The device according to claim 10, wherein said ankle foot orthotic device is provided in a kit comprising modular components comprising different sizes comprising:
    a. said foot support;
    b. said rigid heel plate;
    c. said rod; and
    d. said cuff.

13. The device according to claim 10, wherein said lower surface of said rigid heel plate is configured to connect to an upper surface of a rearward portion of said foot support.

14. The device according to claim 10, wherein said rod is configured to connect to said rigid heel plate, said rod having an upper end configured to have a length sufficient to reach a mid to upper portion of a user's tibia.

15. The device according to claim 10, wherein said rod includes:
    a. a portion extending upwardly from said heel plate and having an upward end connected to an offset; and
    b. an upper rod having a lower end connected to said offset such that said lower end is offset by a distance from said upper end.

16. The device according to claim 15, wherein said offset is configured to allow relative movement along a coronal plane with respect to said foot support.

17. The device according to claim 15, wherein said offset is configured to allow relative movement along a sagittal plane with respect to said foot support.

18. An ankle foot orthotic device for assisting gait, the device comprising:
    a. a foot support having a shape and size configured to the plantar aspect of a user foot, said foot support having a rearward portion and a flexible forward portion;
    b. a rigid heel plate coupled to an upper surface of said rearward portion, wherein:
       i. when a rear end of said heel plate rises with respect to said foot support, and the forward portion is planted on a support surface, energy of bending is transferred beyond the front boundary of said heel plate; and
       ii. when said forward portion is no longer in contact with said support surface, said energy of said bending is transferred such that a sagittal axis passing through said forward portion becomes substantially aligned with a sagittal axis passing through said rearward portion;
c. an upper rod having a longitudinal axis and a lower end connected to an offset;
d. a cuff rotatably connected to an upper end of said upper rod with a rotatable hinge, said rotatable hinge configured to allow a swinging motion in said cuff along a sagittal plane with respect said longitudinal axis of said upper rod;
e. a lower rod having a longitudinal axis extending upwardly from said heel plate and having an upward portion connected to said offset; wherein said offset is configured to allow at least one of:
  i. relative movement along a coronal plane with respect to said foot support; and
  ii. relative movement along a sagittal plane with respect to said foot support.

\* \* \* \* \*